United States Patent
Prawel et al.

(10) Patent No.: US 12,318,510 B2
(45) Date of Patent: Jun. 3, 2025

(54) METHODS AND DEVICES FOR IMPROVING BONE HEALING

(71) Applicant: Colorado State University Research Foundation, Fort Collins, CO (US)

(72) Inventors: David Prawel, Loveland, CO (US); Bernard Seguin, Fort Collins, CO (US); Connor Witt, Colorado Springs, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 437 days.

(21) Appl. No.: 17/541,121

(22) Filed: Dec. 2, 2021

(65) Prior Publication Data

US 2022/0168474 A1 Jun. 2, 2022

Related U.S. Application Data

(60) Provisional application No. 63/120,675, filed on Dec. 2, 2020.

(51) Int. Cl.
| | |
|---|---|
| A61L 27/58 | (2006.01) |
| A61B 17/80 | (2006.01) |
| A61B 17/15 | (2006.01) |
| A61B 17/56 | (2006.01) |

(Continued)

(52) U.S. Cl.
CPC .............. *A61L 27/58* (2013.01); *A61B 17/80* (2013.01); *A61B 17/151* (2013.01); *A61B 2017/568* (2013.01); *A61F 2002/2839* (2013.01); *A61F 2002/30062* (2013.01); *A61F 2002/30677* (2013.01); *A61L 2430/02* (2013.01)

(58) Field of Classification Search
CPC ... A61L 2403/02; A61B 17/151; A61B 17/80; A61B 2017/568; A61F 2002/2839; A61F 2002/30062; A61F 2002/30677
See application file for complete search history.

(56) References Cited

U.S. PATENT DOCUMENTS

| | | | | |
|---|---|---|---|---|
| 5,211,664 | A | * | 5/1993 | Tepic ................... A61L 31/146 623/16.11 |
| 2010/0168771 | A1 | * | 7/2010 | Guldberg ............ A61L 27/3834 606/151 |

(Continued)

OTHER PUBLICATIONS

Abueidda DW et al. Mechanical properties of 3D printed polymeric Gyroid cellular structures: Experimental and finite element study. Materials & Design 2019;165:107597.

(Continued)

*Primary Examiner* — Sameh R Boles
(74) *Attorney, Agent, or Firm* — Robinson IP Law, PLLC

(57) ABSTRACT

A method for treating a bone defect extending between a proximal bone structure and a distal bone structure of a patient may include resecting a region of bone between the proximal bone structure and the distal bone structure and encompassing the bone defect, positioning a biodegradable osteogenic scaffold within a biodegradable sleeve, coupling the biodegradable sleeve to a fixation member, positioning the biodegradable sleeve between the proximal bone structure and the distal bone structure, and attaching the fixation member to each of the proximal bone structure and the distal bone structure.

19 Claims, 9 Drawing Sheets

(51) Int. Cl.
    *A61F 2/28* (2006.01)
    *A61F 2/30* (2006.01)

(56) References Cited

U.S. PATENT DOCUMENTS

2014/0039499 A1* 2/2014 Rose .................. A61L 27/56
                                                        606/74
2019/0209327 A1* 7/2019 Fitzpatrick ............ A61L 27/06

OTHER PUBLICATIONS

Bae J et al. Development and Assessment of a 3D-Printed Scaffold with rhBMP-2 for an Implant Surgical Guide Stent and Bone Graft Material: A Pilot Animal Study. Materials 2017;10:1434.
Bose S et al. Additive manufacturing of biomaterials. Progress in Materials Science 2018;93:45-111.
Boudrieau, R. Initial Experience With thMP-2 Delivered in a Compressive Resistant Matrix for Mandibular Reconstruction in 5 Dogs. Vet Surg 2015;44:443-58.
Brunello G et al. Powder-based 3D printing for bone tissue engineering. Biotechnology Advances 2016;34:740-53.
Choi S et al. New clinical application of three-dimensional-printed polycaprolactone/β-tricalcium phosphate scaffold as an alternative to allograft bone for limb-sparing surgery in a dog with distal radial osteosarcoma. The Journal of Veterinary Medical Science 2019;81:434-9.
El Bialy I et al. Formulation, Delivery and Stability of Bone Morphogenetic Proteins for Effective Bone Regeneration. Pharm Res 2017;34:1152-70.
Eshraghi S et al. Mechanical and microstructural properties of polycaprolactone scaffolds with one-dimensional, two-dimensional, and three-dimensional orthogonally oriented porous architectures produced by selective laser sintering. Acta Biomaterialia 2010;6:2467-76.
Franch J et al. Use of three-dimensionally printed β-TCP synthetic bone graft combined with recombinant human bone morphogenic protein-2 to treat a severe radial atrophic nonunion in a Yorkshire terrier. Veterinary Surgery 2020:vsu.13476.
Grassi Rici R et al. Mesenchymal stem cells with rhBMP-2 inhibits the growth of canine osteosarcoma cells. BMC Vet Res 2012;8:17.
Harrysson Ola et al. Applications of Metal Additive Manufacturing in Veterinary Orthopedic Surgery n.d.:8. 647-654.
Liptak JM et al. Cortical Allograft and Endoprosthesis for Limb-Sparing Surgery in Dogs with Distal Radial Osteosarcoma: A Prospective Clinical Comparison of Two Different Limb-Sparing Techniques. Vet Surgery 2006;35:518-33.
Lissenberg-Thunnissen SN et al. Use and efficacy of bone morphogenetic proteins in fracture healing. International Orthopaedics (SICOT) 2011;35:1271-80.
Lopez Ambrosio, Katherine V. Hydroxyapatite Structures Created by Additive Manufacturing With Extruded Photopolymer. Master's Thesis, Ft. Collins, CO: Colorado State University; 2019.
Lu L et al. Biocompatibility and biodegradation studies of PCL/β-TCP bone tissue scaffold fabricated by structural porogen method. J Mater Sci: Mater Med 2012;23:2217-26.
Melchels FPW et al. Effects of the architecture of tissue engineering scaffolds on cell seeding and culturing. Acta Biomaterialia 2010;6:4208-17.
Melchels FPW et al. Mathematically defined tissue engineering scaffold architectures prepared by stereolithography. Biomaterials 2010;31:6909-16.
Minier K et al. BMP-2 delivered from a self-cross-linkable CaP/hydrogel construct promotes bone regeneration in a critical-size segmental defect model of non-union in dogs. Vet Comp Orthop Traumatol 2014;27:411-21.
Mitchell KE et al. Outcomes of Limb-Sparing Surgery Using Two Generations of Metal Endoprosthesis in 45 Dogs With Distal Radial Osteosarcoma. A Veterinary Society of Surgical Oncology Retrospective Study: Limb Sparing Endoprosthesis for Canine Radial Osteosarcoma. Veterinary Surgery 2016;45:36-43.
Montazerian H et al. Longitudinal and radial permeability analysis of additively manufactured porous scaffolds: Effect of pore shape and porosity. Materials & Design 2017;122:146-56.
Pinel CB, Pluhar GE. Clinical application of recombinant human bone morphogenetic protein in cats and dogs: A review of 13 cases n.d.;53:8.
Rici REG et al. Combination therapy of canine osteosarcoma with canine bone marrow stem cells, bone morphogenetic protein and carboplatin in an in vivo model n.d.:11.
Rodríguez-Montaño ÓL et al. Comparison of the mechanobiological performance of bone tissue scaffolds based on different unit cell geometries. Journal of the Mechanical Behavior of Biomedical Materials 2018;83:28-45.
Seguin B et al. Limb-sparing in dogs using patient-specific, three-dimensional-printed endoprosthesis for distal radial osteosarcoma: A pilot study. Vet Comp Oncol 2020;18:92-104.
Suwanprateeb J et al. Mechanical and in vitro performance of apatite-wollastonite glass ceramic reinforced hydroxyapatite composite fabricated by 3D-printing. J Mater Sci: Mater Med 2009;20:1281.
Vidal L et al. Reconstruction of Large Skeletal Defects: Current Clinical Therapeutic Strategies and Future Directions Using 3D Printing. Front Bioeng. Biotechnol. 2020;8:61.
Vondran et al. 3D printing of ceramic implants. MRS Bulletin 2016;41:71.
Xiong Q et al. BMP-2 inhibits lung metastasis of osteosarcoma: an early investigation using an orthotopic model. OTT 2018; vol. 11:7543-53.
Yuan L et al. Additive manufacturing technology for porous metal implant applications and triple minimal surface structures: A review. Bioactive Materials 2019;4:56-70.

* cited by examiner

METHODS AND DEVICES FOR IMPROVING BONE HEALING

CROSS-REFERENCE TO RELATED APPLICATIONS

This application claims the benefit of, and priority to, U.S. Provisional Patent Application No. 63/120,675, filed on Dec. 2, 2020, and titled "Methods and Devices for Improving Bone Healing," the disclosure of which is expressly incorporated herein by reference in its entirety.

FIELD OF THE DISCLOSURE

The present disclosure relates generally to healing bone defects and more particularly to methods and devices for treating bone defects, such as a critical-sized bone defects, of human or veterinary patients.

BACKGROUND OF THE DISCLOSURE

Critical bone defects occur with unfortunately high frequency in both human veterinary patients, due to cancer and trauma. Poor healing of critical-sized bone defects remains one of the biggest challenges in human and veterinary orthopedic medicine, often resulting in clinical complications, reoperations, poor functional outcomes, and ultimately limb loss, causing significant clinical and economic cost. Researchers have worked on this problem for decades using a wide variety of bone regeneration techniques and biomaterials, often involving 3D printed scaffolds to enhance bone growth, also referred to as bioactivity (osteoconduction, osteoinduction, and osseointegration). Scaffolds made with biomaterials like hydroxyapatite (HAp), beta-tri-calcium phosphate ($\beta$-TCP) and numerous other forms of calcium phosphates and derivatives thereof are highly osteogenic but are too brittle to enable any practical load bearing. Contrarily, enhancing the load-bearing capability of these osteogenic materials results in scaffolds with reduced osteogenic character. To date, no one has overcome this paradox for critical, load-bearing bone defects. The current standard of care for limb-sparing uses permanent fixation with large metal plates and endoprostheses that remain in the patient for lifetime.

Eighty-five percent of all skeletal tumors in dogs are osteosarcomas (see Vail, D. M. et al. Withrow & MacEwen's Small Animal Clinical Oncology. Elsevier Saunders; 2013), most often affecting the proximal humerus and distal radius. Limb-sparing procedures are considered the standard of care in humans. In dogs, limb sparing is indicated in dogs with significant concurrent orthopedic or neurologic disease but is also often performed because the owners are strongly opposed to amputation. These procedures involve ostectomy of the cancerous and surrounding tissue, typically from the diaphysis through and including the epiphysis of the bone, followed by implantation of a large locking fixation plate and endoprosthesis. See Mitchell K E et al. Outcomes of Limb-Sparing Surgery Using Two Generations of Metal Endoprosthesis in 45 Dogs With Distal Radial Osteosarcoma. A Veterinary Society of Surgical Oncology Retrospective Study: Limb Sparing Endoprosthesis for Canine Radial Osteosarcoma. Veterinary Surgery 2016; 45:36-43; Liptak J M et al. Cortical Allograft and Endoprosthesis for Limb-Sparing Surgery in Dogs with Distal Radial Osteosarcoma: A Prospective Clinical Comparison of Two Different Limb-Sparing Techniques. Vet Surgery 2006; 35:518-33. This approach presents complications such as screw loosening, plate fracture, infection, and significant metal remaining in the body for the remainder of the animal's life. These challenges are also experienced in human medicine. Poor healing of these critical-sized bone defects remains one of the biggest challenges in human and veterinary orthopedic surgery, often resulting in limb loss (see Liptak J M et al.), leading to poor long-term outcomes with complication rates as high as 48% in humans (see Vidal L et al. Reconstruction of Large Skeletal Defects: Current Clinical Therapeutic Strategies and Future Directions Using 3D Printing. Front Bioeng. Biotechnol. 2020; 8:61) and over 90% in dogs (see Mitchell K E et al.), reoperations, and poor functional outcomes, resulting in significant negative clinical and economic impact. Other strategies such as autografts, allografts and xenografts also have major drawbacks, including shortage of available tissue, thus there is a critical need to address this challenge. Tissue engineering solutions have emerged that use synthetic scaffolds to provide structure for new growing bone. Countless materials have been considered for scaffold development.

Hydroxyapatite (HAp), beta-tri-calcium phosphate ($\beta$-TCP), and numerous other forms of calcium phosphates and derivatives thereof are widely studied for bone regeneration scaffolds. See Bose S et al. Additive manufacturing of biomaterials. Progress in Materials Science 2018; 93:45-111; Vondran et. al. 3D printing of ceramic implants. MRS Bulletin 2016; 41:71; Suwanprateeb J et al. Mechanical and in vitro performance of apatite-wollastonite glass ceramic reinforced hydroxyapatite composite fabricated by 3D-printing. J Mater Sci: Mater Med 2009; 20:1281. These materials are bioreplaceable by new, native bone. They release calcium during degradation, which supports bone formation, resulting in excellent osteoconductivity. See Vondran et al. Despite excellent bone regeneration properties, success of these scaffolds is hampered by inadequate structural strength and stiffness required for acceptable load-bearing. See Bose S et al. This is especially challenging in critical defects. Polycaprolactone (PCL) is widely used polymeric biomaterial (see Lu L et al. Biocompatibility and biodegradation studies of PCL/$\beta$-TCP bone tissue scaffold fabricated by structural porogen method. J Mater Sci: Mater Med 2012; 23:2217-26) due to its excellent biocompatibility, and is FDA approved for medical use. PCL is popular in bone tissue engineering due to its slow degradation and high stiffness. See Eshraghi S et al. Mechanical and microstructural properties of polycaprolactone scaffolds with one-dimensional, two-dimensional, and three-dimensional orthogonally oriented porous architectures produced by selective laser sintering. Acta Biomaterialia 2010; 6:2467-76; Brunello G et al. Powder-based 3D printing for bone tissue engineering. Biotechnology Advances 2016; 34:740-53. PCL is also radiolucent, enabling real-time radiographic assessment. See Choi S et al. New clinical application of three-dimensional-printed polycaprolactone/$\beta$-tricalcium phosphate scaffold as an alternative to allograft bone for limb-sparing surgery in a dog with distal radial osteosarcoma. The Journal of Veterinary Medical Science 2019; 81:434-9.

3D printing (3DP) has emerged as a popular method to fabricate complex shaped structures with high precision. 3DP enables creation of patient-specific scaffolds directly from CT scans, ensuring the scaffolds precisely fit the defect site, improving outcomes because the morphology of each bone and the percentage of bone removed varies between patients, depending on the size of the tumor. See Harrysson O L A et al. Applications of Metal Additive Manufacturing in Veterinary Orthopedic Surgery n.d.:8; Seguin B et al.

Limb-sparing in dogs using patient-specific, three-dimensional-printed endoprosthesis for distal radial osteosarcoma: A pilot study. Vet Comp Oncol 2020; 18:92-104. Patient-specific implants allow the implants to fit as perfectly as possible for each patient thereby enabling loads to be transmitted through the limb. Interrelated parameters such as porosity, permeability, pore size, shear stress, bulk material, and shape (topology) dictate the success of a scaffold. See Montazerian H et al. Longitudinal and radial permeability analysis of additively manufactured porous scaffolds: Effect of pore shape and porosity. Materials & Design 2017; 122:146-56; Rodriguez-Montaño Ó L et al. Comparison of the mechanobiological performance of bone tissue scaffolds based on different unit cell geometries. Journal of the Mechanical Behavior of Biomedical Materials 2018; 83:28-45; Abueidda D W et al. Mechanical properties of 3D printed polymeric Gyroid cellular structures: Experimental and finite element study. Materials & Design 2019; 165:107597; Melchels F P W et al. Effects of the architecture of tissue engineering scaffolds on cell seeding and culturing. Acta Biomaterialia 2010; 6:4208-17. Advanced, structurally-optimized scaffold topologies such as Gyroids (see Montazerian H et al.; Melchels F P W et al. Mathematically defined tissue engineering scaffold architectures prepared by stereolithography. Biomaterials 2010; 31:6909-16) are enabling 3D printing of stiffer, stronger scaffolds (see Rodriguez-Montaño Ó L et al.; Abueidda D W et al.; Yuan L et al. Additive manufacturing technology for porous metal implant applications and triple minimal surface structures: A review. Bioactive Materials 2019; 4:56-70).

Recombinant human bone morphogenic protein-2 (rhBMP-2) is one of the most widely used growth factors in both human (see Lissenberg-Thunnissen S N et al. Use and efficacy of bone morphogenetic proteins in fracture healing. International Orthopaedics (SICOT) 2011; 35:1271-80) and veterinary (see Pinel C B, Pluhar G E. Clinical application of recombinant human bone morphogenetic protein in cats and dogs: A review of 13 cases n.d.; 53:8; Boudrieau, R. Initial Experience With rhBMP-2 Delivered in a Compressive Resistant Matrix for Mandibular Reconstruction in 5 Dogs. Vet Surg 2015; 44:443-58) orthopedic surgery because of its powerful osteoinductive properties. A suitable carrier is required for sustained and local delivery of rhBMP-2. See El Bialy I et al. Formulation, Delivery and Stability of Bone Morphogenetic Proteins for Effective Bone Regeneration. Pharm Res 2017; 34:1152-70. Various forms of calcium phosphate have proven successful in numerous BMP delivery systems for large defect bone healing. Despite some reports of hypertrophy observed in some experimental (see Minier K et al. BMP-2 delivered from a self-cross-linkable CaP/hydrogel construct promotes bone regeneration in a critical-size segmental defect model of non-union in dogs. Vet Comp Orthop Traumatol 2014; 27:411-21) and clinical (see Pinel C B et al.; Boudrieau R et al) cases treated with rhBMP-2, recent studies counter that RhBMP-2 can have anti-neoplastic effects against osteosarcoma (see Xiong Q et al. BMP-2 inhibits lung metastasis of osteosarcoma: an early investigation using an orthotopic model. OTT 2018; Volume 11:7543-53; Rici R E G et al. Combination therapy of canine osteosarcoma with canine bone marrow stem cells, bone morphogenetic protein and carboplatin in an in vivo model n.d.:11; Grassi Rici R et al. Mesenchymal stem cells with rhBMP-2 inhibits the growth of canine osteosarcoma cells. BMC Vet Res 2012; 8:17).

Although existing techniques for treating bone defects may be suitable in certain applications, there remains a need for improved methods and devices for treating bone defects, such as a critical-sized bone defects, of human or veterinary patients, which may overcome one or more of the drawbacks associated with existing techniques

SUMMARY OF THE DISCLOSURE

The present disclosure provides methods and devices for treating bone defects, such as a critical-sized bone defects, of human or veterinary patients. In one aspect, a method for treating a bone defect extending between a proximal bone structure and a distal bone structure of a patient is provided. In one embodiment, the method may include resecting a region of bone between the proximal bone structure and the distal bone structure and encompassing the bone defect, positioning a biodegradable osteogenic scaffold within a biodegradable sleeve, coupling the biodegradable sleeve to a fixation member, positioning the biodegradable sleeve between the proximal bone structure and the distal bone structure, and attaching the fixation member to each of the proximal bone structure and the distal bone structure.

In some embodiments, coupling the biodegradable sleeve to the fixation member may include sliding the biodegradable sleeve onto the fixation member. In some embodiments, positioning the biodegradable sleeve between the proximal bone structure and the distal bone structure may include inserting a distal end portion of the proximal bone structure into a proximal end of the biodegradable sleeve such that the distal end portion contacts the biodegradable osteogenic scaffold, and inserting a proximal end portion of the distal bone structure into a distal end of the biodegradable sleeve such that the proximal end portion contacts the biodegradable osteogenic scaffold. In some embodiments, attaching the fixation member to each of the proximal bone structure and the distal bone structure may include attaching the fixation member to the proximal bone structure using a first plurality of screws, and attaching the fixation member to the distal bone structure using a second plurality of screws. In some embodiments, the method also may include treating the biodegradable osteogenic scaffold with one or more bioactive agents to facilitate bone growth or angiogenesis. In some embodiments, the method also may include treating the biodegradable sleeve and the fixation member with an antibiotic to inhibit infection. In some embodiments, the method also may include obtaining computed tomography scans of the patient, and fabricating the biodegradable osteogenic scaffold and the biodegradable sleeve based at least in part on the computed tomography scans. In some embodiments, the method also may include fabricating a cutting guide based at least in part on the computed tomography scans, and resecting the region of bone between the proximal bone structure and the distal bone structure and encompassing the bone defect may include resecting the region of bone using the cutting guide. In some embodiments, the biodegradable osteogenic scaffold may be formed of a calcium phosphate-based material or a composite comprising a calcium phosphate and a polymer, and the biodegradable sleeve may be formed of polycaprolactone or a composite comprising a calcium phosphate and polycaprolactone. In some embodiments, the method also may include detaching the fixation member from the proximal bone structure and the distal bone structure and removing the fixation member from the patient after the bone defect has healed and the biodegradable osteogenic scaffold and the biodegradable sleeve have degraded.

In another aspect, a device for treating a bone defect extending between a proximal bone structure and a distal bone structure of a patient is provided. In one embodiment, the device may include a biodegradable sleeve configured for positioning between the proximal bone structure and the distal bone structure, a biodegradable osteogenic scaffold configured for positioning within the biodegradable sleeve, and a fixation member configured for coupling to the biodegradable sleeve and attaching to each of the proximal bone structure and the distal bone structure.

In some embodiments, the biodegradable sleeve may include a first passage extending from a proximal end to a distal end of the biodegradable sleeve and configured for receiving the biodegradable osteogenic scaffold therein, and a second passage extending from the proximal end to the distal end of the biodegradable sleeve and configured for receiving a portion of the fixation member therein. In some embodiments, the biodegradable sleeve also may include support ribs disposed between the first passage and the second passage and extending from the proximal end to the distal end of the biodegradable sleeve, and the first passage may be in communication with the second passage through a gap defined between the ribs. In some embodiments, a portion of the biodegradable osteogenic scaffold may extend into the gap when the biodegradable osteogenic scaffold is positioned within the biodegradable sleeve. In some embodiments, the first passage also may be configured for receiving a distal end portion of the proximal bone structure and a proximal portion of the distal bone structure therein. In some embodiments, the biodegradable sleeve also may include a plurality of apertures disposed along one or more sides of the biodegradable sleeve and extending from an outer surface of the biodegradable sleeve to the first passage, and the apertures may be configured for controlling transcortical perfusion. In some embodiments, the biodegradable sleeve also may include a plurality of openings disposed along a side of the biodegradable sleeve and extending from an outer surface of the biodegradable sleeve to the second passage, and the openings may expose respective portions of the fixation member when the fixation member is coupled to the biodegradable sleeve and may be configured for receiving respective collagen sponges carrying an antibiotic therein. In some embodiments, the biodegradable osteogenic scaffold may include a central passage extending from a proximal end to a distal end of the biodegradable osteogenic scaffold and configured for receiving a collagen sponge carrying rhBMP-2 or vascular endothelial growth factor (VEGF) therein. In some embodiments, the fixation member may include a proximal portion configured for extending beyond the proximal end of the biodegradable sleeve when the fixation member is coupled to the biodegradable sleeve, a distal portion configured for extending beyond the distal end of the biodegradable sleeve when the fixation member is coupled to the biodegradable sleeve, and an intermediate portion configured for positioning within the second passage when the fixation member is coupled to the biodegradable sleeve. In some embodiments, the biodegradable osteogenic scaffold may be formed of a calcium phosphate-based material or a composite comprising a calcium phosphate and a polymer, and the biodegradable sleeve may be formed of polycaprolactone or a composite comprising a calcium phosphate and polycaprolactone.

These and other aspects and improvements of the present disclosure will become apparent to one of ordinary skill in the art upon review of the following detailed description when taken in conjunction with the several drawings and the appended claims.

Figure 1A:
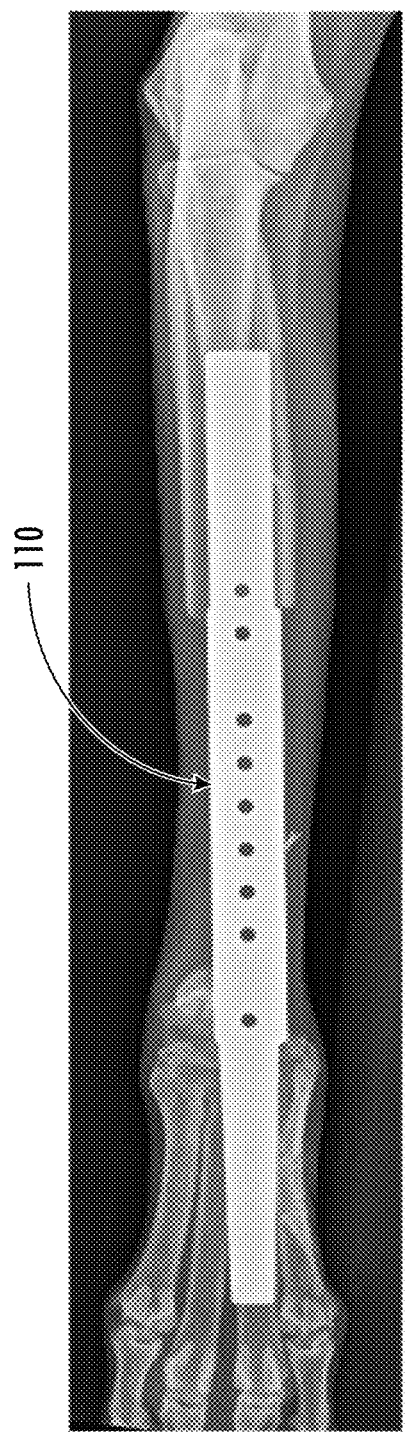
FIG. 1A is a top view radiograph of a current standard of care for treating a critical bone defect in a limb-sparing procedure, showing a metal locking plate.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and/or components have not been described in detail so as not to unnecessarily obscure aspects of the embodiments.

Overview

Embodiments of methods and devices for treating a bone defect, such as a critical-sized bone defect, extending between a proximal bone structure and a distal bone structure of a patient are provided. As described herein, example methods generally may include resecting a region of bone between the proximal bone structure and the distal bone structure and encompassing the bone defect, positioning a biodegradable osteogenic scaffold within a biodegradable sleeve, coupling the biodegradable sleeve to a fixation member, positioning the biodegradable sleeve between the proximal bone structure and the distal bone structure, and attaching the fixation member to each of the proximal bone structure and the distal bone structure. In this manner, the fixation member may provide fixation of the proximal bone structure and the distal bone structure across the bone defect to enable normal load bearing, the biodegradable osteogenic scaffold may facilitate new bone growth between the proximal bone structure and the distal bone structure, and the biodegradable sleeve may protect the biodegradable osteogenic scaffold while new bone grows and also contain the new bone growth. Over time, the biodegradable osteogenic scaffold and the biodegradable sleeve may degrade, the new, natural bone growth may provide complete bone healing between the proximal bone structure and the distal bone structure, and the fixation member may be removed from the patient, leaving only endogenous bone. As described herein, example devices generally may include a biodegradable sleeve configured for positioning between the proximal bone structure and the distal bone structure, a biodegradable osteogenic scaffold configured for positioning within the biodegradable sleeve, and a fixation member configured for coupling to the biodegradable sleeve and attaching to each of the proximal bone structure and the distal bone structure. Various configurations of the device components may be used in different embodiments.

The present disclosure provides endoprosthetic designs and surgical procedures that can be used in veterinary and human orthopedic medicine. As discussed above, HAp, β-TCP, and numerous other forms of calcium phosphates and derivatives thereof are excellent and widely used biomaterial for bone regeneration but provide insufficient mechanical support for acceptable load bearing. Many researchers are succeeding at strengthening such scaffolds using a wide variety of additives and infiltration techniques, but thus far at the cost of reductions in bioactivity. The methods and devices described herein leverage the fixation member to support the load, as it already functions in the current standard of care, and as a means to connect to and protect an osteogenic calcium-phosphate-based scaffold so that the scaffold can enable new bone growth and bioactivity. A critical-sized, patient-specific, biodegradable endoprostheses may be 3D printed to protect the scaffold and augment its poor mechanical properties, while working alongside the fixation member. The scaffold may be treated with rhBMP-2 to enhance bone healing, as recently demonstrated for large bone defects (see Grassi Rici R et al. Mesenchymal stem cells with rhBMP-2 inhibits the growth of canine osteosarcoma cells. BMC Vet Res 2012; 8:17; Franch J et al. Use of three-dimensionally printed β-TCP synthetic bone graft combined with recombinant human bone morphogenic protein-2 to treat a severe radial atrophic nonunion in a Yorkshire terrier. Veterinary Surgery 2020: vsu.13476). As described, the present techniques in limb sparing treatment of a bone defect, based on current standard of care, use bioreplaceable endoprostheses to enable a highly osteogenic scaffold to support healthy bone growth under normal loads. Ultimately, the techniques can enable complete bone healing and removal of fixation, leaving the patient with endogenous bone as in the Franch study (see Franch J et al.), after the endoprostheses degrades safely in the body.

Although initial development of the disclosed methods and devices has been performed in dogs, the methods and devices translate to human medicine fairly easily. The dog is a highly suitable model for human bone from a biological standpoint, in many ways better than sheep (see Bae J et al. Development and Assessment of a 3D-Printed Scaffold with rhBMP-2 for an Implant Surgical Guide Stent and Bone Graft Material: A Pilot Animal Study. Materials 2017; 10:1434), with similarities in microstructure and remodeling. Large dogs weigh as much as a small to mid-sized human. Furthermore, the techniques described herein depend on structural design improvements rather than complex physiological or biological approaches, that translate more readily to human medicine. Medical devices for canine orthopedics are often identical to those for humans, making possible translation of devices. Materials used for the scaffold and endoprostheses have been thoroughly studied and known to be biocompatible for implantation in live animals and FDA approved for many applications. The disclosed methods and devices can significantly improve patient outcomes in limb-sparing procedures, for animals and humans alike.

Figure 1B:
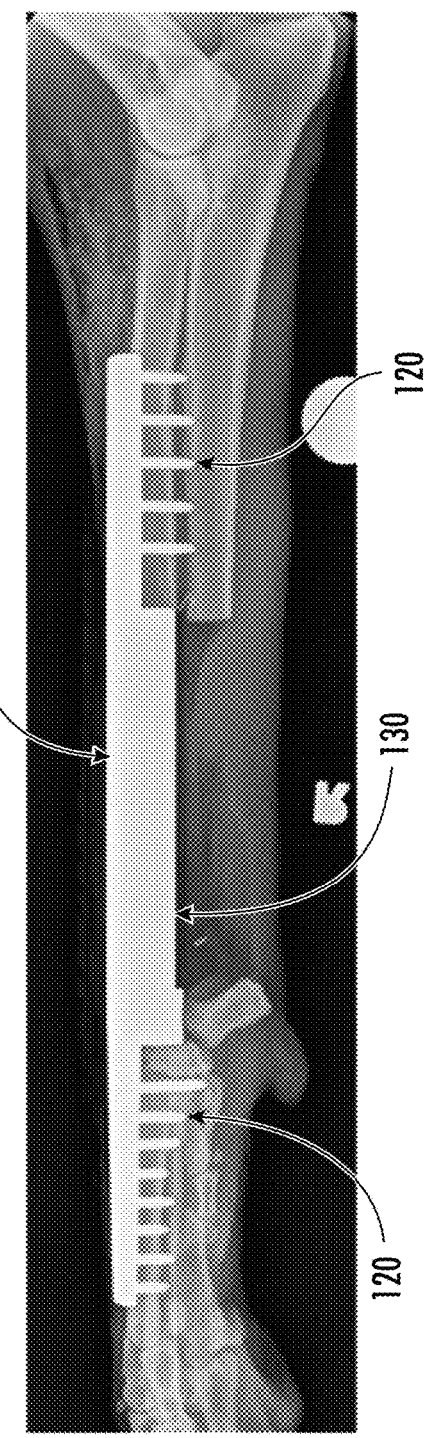
FIG. 1B is a side view radiograph of a current standard of care for treating a critical bone defect in a limb-sparing procedure, showing a metal locking plate, screws, and an endoprosthetic spacer.

FIGS. 1A and 1B illustrate one instance of a standard of care for treating a bone defect, specifically an epiphyseal defect in a limb of a canine patient being treated for osteosarcoma. In this case, as shown, a distal portion of the patient's radius encompassing the tumor may be removed, along with a distal portion of the patient's ulna. Fixation of the limb may be provided by a metal locking plate 110 that is attached via screws 120 to each of a proximal bone structure and a distal bone structure. As shown, a proximal end portion of the locking plate 110 may be attached to the remaining host radius, and a distal end portion of the locking plate 110 may be attached to the third metacarpal. An endoprosthesis 130 may be positioned between the proximal bone structure and the distal bone structure to act as a spacer for limiting movement of the proximal bone structure relative to the distal bone structure to inhibit loosening of the locking plate 110. As shown, the endoprosthesis 130 may be positioned between the remaining host radius and the radial carpus. Although the depicted example shows the locking plate 110, the screws 120, and the endoprosthesis 130 being used to treat an epiphyseal defect, these components similarly may be used to treat a segmental defect in a limb of a patient. As discussed above, the standard of care approach may present certain complications, including screw loosening, plate fracture, infection, and significant metal remaining in the body for the remainder of the patient's life.

Example Devices and Methods for Treating a Bone Defect

Figure 2A:
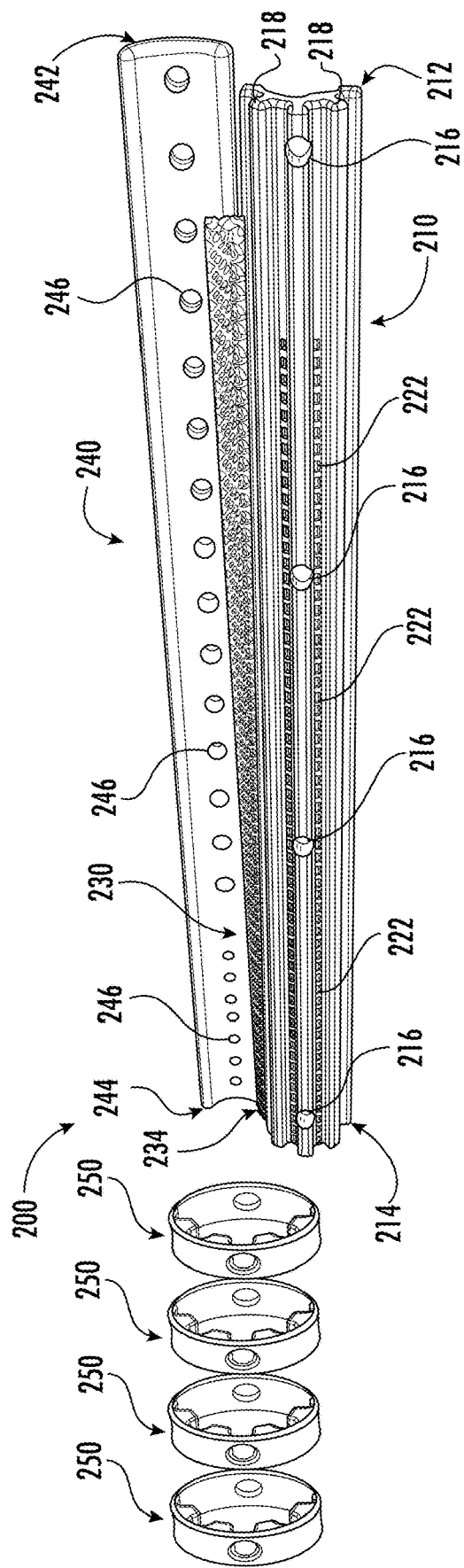
FIG. 2A is an exploded perspective view of an example device for treating a bone defect in accordance with embodiments of the disclosure, showing a biodegradable sleeve, a biodegradable osteogenic scaffold, a fixation member, and a plurality of biodegradable cuffs of the device.
Figure 2B:
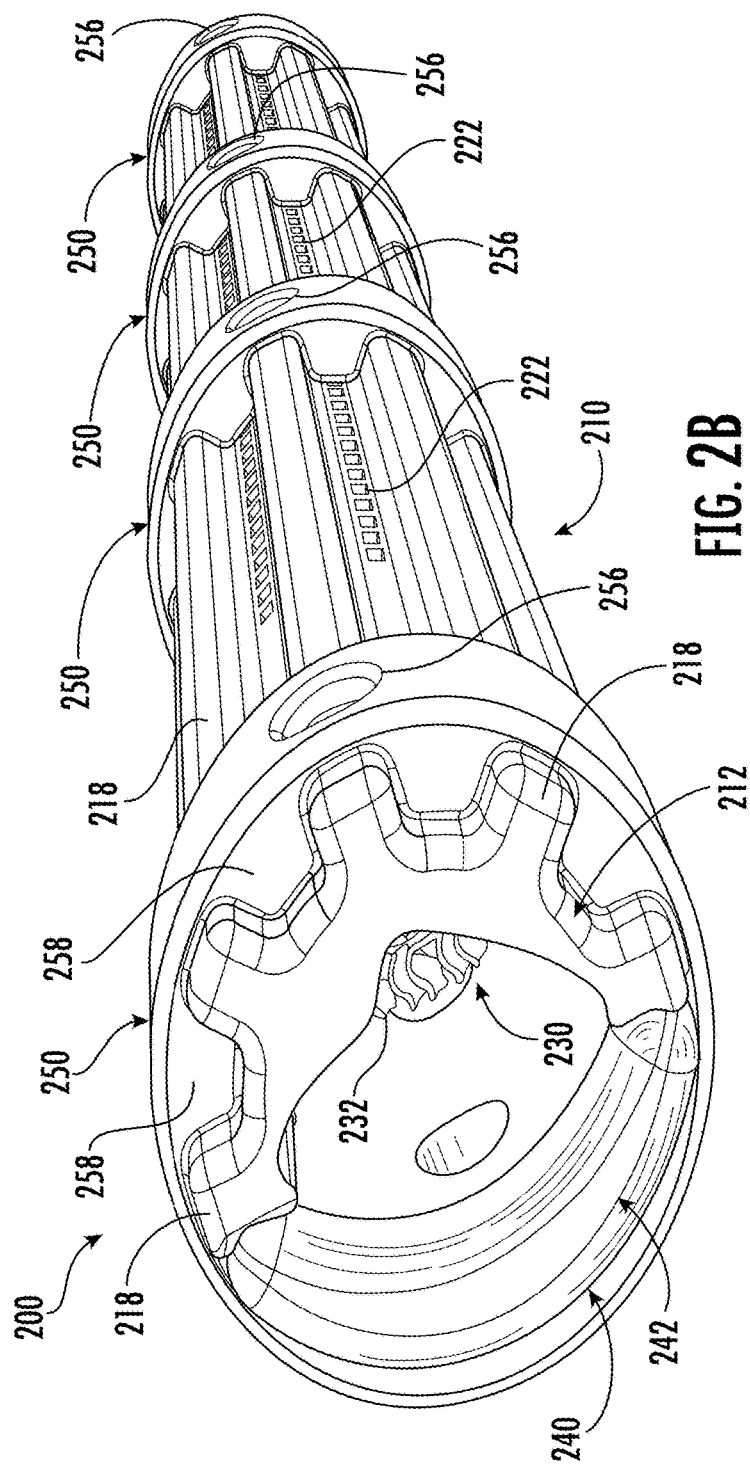
FIG. 2B is a perspective view of the device of FIG. 2A, showing the biodegradable sleeve, the biodegradable osteogenic scaffold, the fixation member, and the biodegradable cuffs in an assembled state.
Figure 2C:
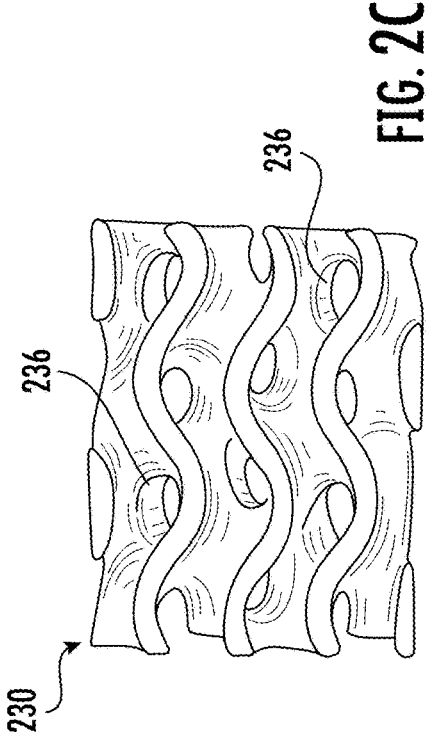
FIG. 2C is a detailed side view of a portion of the biodegradable osteogenic scaffold, showing a gyroid topology of the scaffold.

FIGS. 2A-2C illustrate an example device 200 for treating a bone defect, such as a critical-sized bone defect, of a veterinary or human patient. In some instances, the device 200 may be used to treat an epiphyseal defect. In other instances, the device 200 may be used to treat a segmental defect, a mandibular defect, or other type of bone defect. As shown, the device 200 may include a biodegradable sleeve 210, a biodegradable osteogenic scaffold 230, a fixation member 240, and a plurality of biodegradable cuffs 250. It will be appreciated that the size and shape of the respective components of the device 200 may be varied to accommodate a particular patient and the particular defect being treated. As discussed below, in some embodiments, the biodegradable sleeve 210, the biodegradable osteogenic scaffold 230, and the biodegradable cuffs 250 may be fabricated as patient-specific components. For example, these components may be 3D printed based on CT scans of the patient's limb. In some embodiments, the fixation member 240 may be a commercially-available component used in accordance with the standard of care, with the size of the fixation member 240 being selected to accommodate the patient and defect to be treated.

As shown, the biodegradable sleeve 210 may be formed as an elongate structure having a proximal end 212 and a distal end 214 disposed opposite one another along the longitudinal axis of the biodegradable sleeve 210. In some embodiments, as shown, the proximal end 212 may be shape-matched to a distal portion of the proximal bone structure of the patient, and the distal end 214 may be shape matched to a proximal portion of the distal bone structure of the patient. For example, for an epiphyseal defect, the proximal end 212 may be shape-matched to the remaining host radius, and the distal end 214 may be shape-matched to the radial carpus. In some embodiments, as shown, the biodegradable sleeve 210 may have a generally C-shaped cross-sectional shape (i.e., taken perpendicular to the longitudinal axis of the biodegradable sleeve 210), with a gap extending along one side of the biodegradable sleeve 210. In this manner, the biodegradable sleeve 210 may include a passage configured for receiving the biodegradable osteogenic scaffold 230 therein during use of the device 200. In some embodiments, as shown, the biodegradable sleeve 210 may include a plurality of screw holes 216 extending therethrough and spaced apart from one another along the length of the biodegradable sleeve 210. As discussed below, the screw holes 216 may facilitate connection of the biodegradable sleeve 210 to the fixation member 240 and the biodegradable cuffs 250. In some embodiments, as shown, the biodegradable sleeve 210 may include a plurality of ribs 218 each extending from the proximal end 212 to the distal end 214. As discussed below, the ribs 218 may facilitate connection of the biodegradable sleeve 210 to the biodegradable cuffs 250 and load sharing therebetween. In some embodiments, as shown, the biodegradable sleeve 210 may include a plurality of apertures 222 extending therethrough and spaced apart from one another along the length of the biodegradable sleeve 210. The apertures 222 may be configured for controlling transcortical perfusion during use of the device 200. In some embodiments, the apertures 222 may be omitted to prevent transcortical perfusion through the biodegradable sleeve 210. In some embodiments, the biodegradable sleeve 210 may be formed of polycaprolactone or a composite comprising a calcium phosphate and polycaprolactone. Other suitable biocompatible and biodegradable materials may be used for the biodegradable sleeve 210 in other embodiments.

The biodegradable osteogenic scaffold 230 may be formed as an elongate structure having a proximal end 232 and a distal end 234 disposed opposite one another along the longitudinal axis of the biodegradable osteogenic scaffold 230. In some embodiments, as shown, the biodegradable osteogenic scaffold 230 may have a gyroid topology, with a plurality of interconnected pores 236. Other porous topologies of the biodegradable osteogenic scaffold 230 may be used in other embodiments. In some embodiments, the biodegradable osteogenic scaffold 230 may have a porosity of 70%. In some embodiments, the biodegradable osteogenic scaffold 230 may include a hollow canal configured for allowing intracortical perfusion. As shown, the length of the biodegradable osteogenic scaffold 230 may be less than the length of the biodegradable sleeve 210. In this manner, the biodegradable osteogenic scaffold 230 may be positioned entirely within the biodegradable sleeve 210 during use of the device 200. In some embodiments, the biodegradable osteogenic scaffold 230 may be formed of a calcium phosphate, such as HAp or β-TCP. In some embodiments, the biodegradable osteogenic scaffold 230 may be formed of a calcium phosphate-based material or a composite comprising a calcium phosphate and a polymer. Other suitable biocompatible, biodegradable, and osteogenic materials may be used for the biodegradable osteogenic scaffold 230 in other embodiments.

The fixation member 240 may be formed as an elongate structure having a proximal end 242 and a distal end 244 disposed opposite one another along the longitudinal axis of the fixation member 240. According to various embodiments, the fixation member 240 may be a fixation plate, a fixation rod, a locking plate, a locking rod, or other type of suitable structure for fixation of bone structures. In some embodiments, as shown, the fixation member 240 may have a curved cross-sectional shape (i.e., taken perpendicular to the longitudinal axis of the fixation member 240). As discussed below, the fixation member 240 may be coupled to the biodegradable sleeve 210 such that the fixation member 240 covers the open side of the biodegradable sleeve 210, thereby containing the biodegradable osteogenic scaffold 230 between the fixation member 240 and the biodegradable sleeve 210. In some embodiments, as shown, the fixation member 240 may be inserted into the gap of the biocompatible sleeve 210. As shown, the fixation member 240 may include a plurality of screw holes 246 extending therethrough and spaced apart from one another along the length of the fixation member 240. As discussed below, some of the screw holes 246 may be used to facilitate connection of the fixation member 240 to the biodegradable sleeve 210 and the biodegradable cuffs 250, while other screw holes 246 may be used to facilitate connection of the fixation member 240 to a proximal bone structure and a distal bone structure during use of the device 200. The fixation member 240 may be formed of any suitable biocompatible, non-biodegradable material such that the fixation member 240 may be removed from the patient after the bone defect has healed and the biodegradable sleeve 210 and the biodegradable osteogenic scaffold 230 have degraded. According to various embodiments, the fixation member 240 may be formed of a metal, a polymeric material, a ceramic material, a composite material, or other suitable material for fixation of bone structures.

As shown, each of the biodegradable cuffs 250 may be formed as ring-shaped members configured for sliding over the biodegradable sleeve 210 and the fixation member 240. In some embodiments, as shown, edges of the biodegradable sleeve 210 and the fixation member 240 may be rounded to ease sliding of the biodegradable cuffs 250 onto the biodegradable sleeve 210 and the fixation member 240 as well as to minimize tissue trauma. In some embodiments, as shown, each of the biodegradable cuffs 250 may include a pair of screw holes 256 extending therethrough and disposed opposite one another. The screw holes 256 may facilitate connection of each of the biodegradable cuffs 250 to the biodegradable sleeve 210 and the fixation member 240. In some embodiments, as shown, for each of the biodegradable cuffs 250, a screw may be inserted through one of the screw holes 256 of the biodegradable cuff 250, through one of the screw holes 246 of the fixation member 240, through the biocompatible osteogenic scaffold 230, through one of the screw holes 216 of the biodegradable sleeve 210, and through the other screw hole 256 of the biodegradable cuff 250. This configuration may distribute load through the biodegradable cuff 250 into the fixation member 240, which may maintain the integrity and minimize mobility of the biocompatible osteogenic scaffold 230 as new bone develops. In some embodiments, as shown, each of the biodegradable cuffs 250 may include a plurality of protrusions 258 extending radially inward and configured for mating with the ribs 218 of the biodegradable sleeve 210. As shown, the mating engagement between the protrusions 258 and the ribs 218 may facilitate alignment of the screw holes 256 of the biodegradable cuff 250 with the screw holes 216 of the biodegradable sleeve 210 and the screw holes 246 of the fixation member 240. In some embodiments, the biodegradable cuffs 250 may be formed of polycaprolactone or a composite comprising a calcium phosphate and polycaprolactone. Other suitable biocompatible and biodegradable materials may be used for the biodegradable cuffs 250 in other embodiments.

As noted above, the biodegradable sleeve 210, the biodegradable osteogenic scaffold 230, and the biodegradable cuffs 250 may be fabricated as patient-specific components. In some embodiments, CT scans of the patient's limb may be used to fabricate the biodegradable sleeve 210, the biodegradable osteogenic scaffold 230, and the biodegradable cuffs 250 for the patient. In some embodiments, a series of two-dimensional DICOM images of the full extent of the limb may be imported (e.g., using InVesalius) and segmented to create high-resolution digital models of the radius, ulna, manus, and metacarpals of the patient. The images then may be segmented based on Hounsfield attenuation values, and surface representations of the bone may be generated and then imported (e.g., into Fusion 360) where 3D models of the components may be created for 3D printing. In some embodiments, finite element analysis (FEA) may be used to investigate the ideal design parameters of the biodegradable sleeve 210 and the biodegradable cuffs 250 and the overall device 200, with and without the fixation member 240, to determine optimal geometry of the components and features thereof. Parameters such as rib height and thickness and mechanical properties such as structural modulus may be simulated to optimize the design of the device 200 prior to fabrication. In some embodiments, the CT scans also may be used to fabricate cutting guides to assure accurate surgical resections to match the geometry of the device 200.

The biodegradable osteogenic scaffold 230 may be 3D printed using existing methods. See Lopez Ambrosio, Katherine V. HYDROXYAPATITE STRUCTURES CREATED BY ADDITIVE MANUFACTURING WITH EXTRUDED PHOTOPOLYMER. Master's Thesis, Ft. Collins, CO: Colorado State University; 2019; 2019. In some embodiments, a photopolymer comprised of ethylene glycol dimethacrylate (EDGMA) and other polymers may be mixed with hydroxyapatite (HAp) particles into a shear-thinning slurry using a planetary ball mill. Slurries of 41 vol % HAp may be transferred to a syringe and 3D printed on 3D printer, such as a HyRel Engine SR printer with a 0.413 mm nozzle inner diameter, using a combination of viscous extrusion and photopolymer processes. The photopolymerization reaction may be initiated by continuous exposure of the deposited roads to a near-UV light source (405 nm wavelength), causing polymerization and hardening of the continuous phase, layer-by-layer. The sintered biodegradable osteogenic scaffold 230 may be non-cytotoxic. After printing, the biodegradable osteogenic scaffold 230 may undergo a two-step sintering process to eliminate the polymeric content and consolidate the HAp particles. In some embodiments, the printed biodegradable osteogenic scaffold 230 may be heated at 5° C./min up to 500° C. and held for 1 h, and then sintered at a heating rate of 15° C./min, up to 1150° C. and held for 5 h. This process may confer the sintered HAp structures with suitable mechanical properties. In some embodiments, the biodegradable sleeve 210 and the biodegradable cuffs 250 may be fabricated using a thermal process on a melt extrusion 3D printer (e.g., Prusa i3-MK3, Budapest, Hungary). PCL filament may be extruded by regulated ram pressure through a Flexion head. The extruded PCL may cool on a build plate to fabricate the components, which then may cool to room temperature. Prints may be oriented to maximize part strength and minimize support material.

The device 200 may be used to treat a bone defect, such as a critical-sized bone defect, extending between a proximal bone structure and a distal bone structure of a patient. In some embodiments, the bone defect may be an epiphyseal defect. In some embodiments, the bone defect may be a segmental defect. A method of using the device 200 for treating the bone defect generally may include resecting a region of bone between the proximal bone structure and the distal bone structure and encompassing the bone defect, positioning the biodegradable osteogenic scaffold 230 within the biodegradable sleeve 210, coupling the biodegradable sleeve 210 to the fixation member 240, positioning the biodegradable sleeve 210 between the proximal bone structure and the distal bone structure, and attaching the fixation member 240 to each of the proximal bone structure and the distal bone structure.

In some embodiments, the region of bone may be resected using one or more cutting guides fabricated based on CT scans of the patient's limb. For an epiphyseal defect, approximately 40% of the distal radius may be removed, along with a slightly larger section of the ulna to enable insertion of the device 200. In some embodiments, the biodegradable osteogenic scaffold 230 may be treated with one or more bioactive agents to facilitate bone growth or angiogenesis before positioning the biodegradable osteogenic scaffold 230 within the biodegradable sleeve 210. For example, the biodegradable osteogenic scaffold 230 may be treated with rhBMP-2 to facilitate bone growth and/or vascular endothelial growth factor (VEGF) to facilitate angiogenesis. In some embodiments, the biodegradable osteogenic scaffold 230 may be positioned within the biodegradable sleeve 210 such that the proximal end 232 of the biodegradable osteogenic scaffold 230 is offset from the proximal end 212 of the biodegradable sleeve 210, and a distal portion of the proximal bone structure may be inserted into the biodegradable sleeve 210 and in contact with the proximal end 232 of the biodegradable osteogenic scaffold 230. For an epiphyseal defect, a distal portion of the remaining host radius may be inserted into the biodegradable sleeve 210 and in contact with the proximal end 232 of the biodegradable osteogenic scaffold 230. In some embodiments, the biodegradable osteogenic scaffold 230 may be positioned within the biodegradable sleeve 210 such that the distal end 234 of the biodegradable osteogenic scaffold 230 is flush with the distal end 214 of the biodegradable sleeve 210, and a proximal portion of the distal bone structure may be positioned in close contact with the distal end 234 of the biodegradable osteogenic scaffold 230 and the distal end 214 of the biodegradable sleeve 210. For an epiphyseal defect, the proximal end of the carpus may be positioned in close contact with the distal end 234 of the biodegradable osteogenic scaffold 230 and the distal end 214 of the biodegradable sleeve 210. In some embodiments, the biodegradable osteogenic scaffold 230 may be positioned within the biodegradable sleeve 210 such that the distal end 234 of the biodegradable osteogenic scaffold 230 is offset from the distal end 214 of the biodegradable sleeve 210, and a proximal portion of the distal bone structure may be inserted into the biodegradable sleeve 210 and in contact with the distal end 234 of the biodegradable osteogenic scaffold 230.

In some embodiments, the biodegradable sleeve 210 may be coupled to the fixation member 240 before the biodegradable sleeve 210 is positioned between the proximal bone structure and the distal bone structure. In some embodiments, the biodegradable sleeve 210 may be coupled to the fixation member 240 by inserting the fixation member 240 into the gap of the biodegradable sleeve 210. In some embodiments, a proximal end portion of the fixation member 240 may be attached to the proximal bone structure using a first plurality of screws, and a distal end portion of the fixation member 240 may be attached to the distal bone structure using a second plurality of screws. For an epiphyseal defect, the proximal end portion of the fixation member 240 may be attached to the remaining host radius, and the distal end portion of the fixation member 240 may be attached to the third metacarpal.

In some embodiments, the biodegradable cuffs 250 may be slid over the biodegradable sleeve 210 and the fixation member 240 after the fixation member 240 is attached to the proximal bone structure but before the fixation member 240 is attached to the distal bone structure. One of the biodegradable cuffs 250 may be slid over the biodegradable sleeve 210 and the fixation member 240 from the distal ends 214, 244 toward the proximal ends 212, 242 thereof, aligned with the proximal-most screw hole 216 of the biodegradable sleeve 210, and connected to the biodegradable sleeve 210 and the fixation member 240 using a screw. The screw may pass through the biodegradable cuff 250, the fixation member 240, and the bone cortex of the proximal bone structure on the cis side and through the bone cortex of the proximal bone structure, the biodegradable sleeve 210, and the biodegradable cuff 250 on the trans side. In this manner, the screw may lock the proximal end of the device 200 into position. The screw should not protrude exceedingly far from the biodegradable cuff 250 to minimize risk of collateral tissue trauma. Each of the remaining biodegradable cuffs 250 then may be slid over the biodegradable sleeve 210 and the fixation member 240 from the distal ends 214, 244 toward the proximal ends 212, 242 thereof, aligned with one of the remaining screw holes 216 of the biodegradable sleeve 210, and connected to the biodegradable sleeve 210 and the fixation member 240 using a respective screw. Each of these screws may pass through the biodegradable cuff 250, the fixation member 240, the biodegradable osteogenic scaffold 230, the biodegradable sleeve 210, and the biodegradable cuff 250. After connecting the biodegradable cuffs 250, the distal end 214 of the biodegradable sleeve 210 and the distal end of the biodegradable osteogenic scaffold 230 may be positioned in close contact with a proximal portion of the distal bone structure, and the distal end portion of the fixation member 240 may be attached to the distal bone structure. For an epiphyseal defect, the distal end 214 of the biodegradable sleeve 210 and the distal end of the biodegradable osteogenic scaffold 230 may be positioned in close contact with the proximal end of the carpus, and the distal end portion of the fixation member 240 may be attached to the third metacarpal.

Figure 3A:
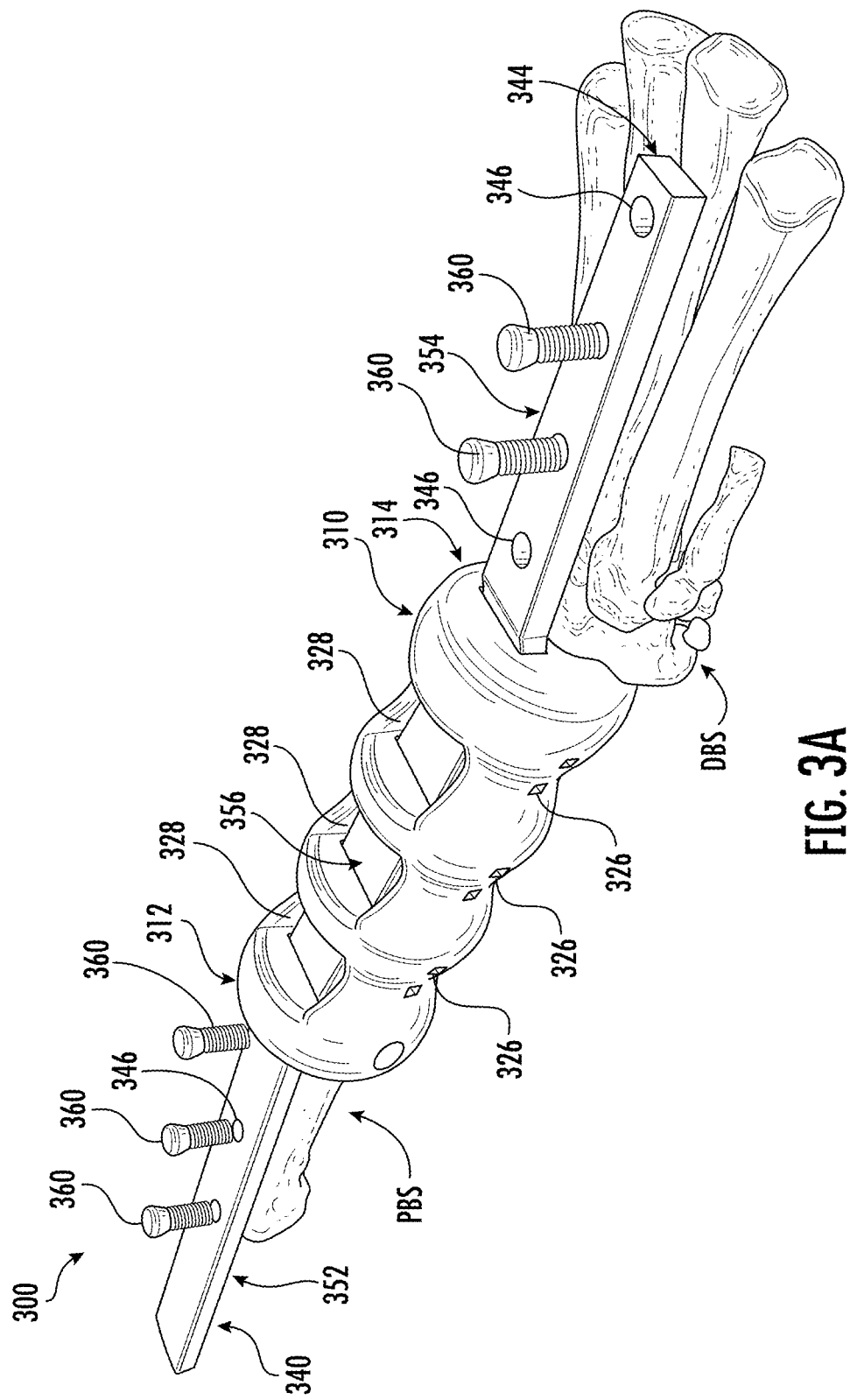
FIG. 3A is a perspective view of an example device for treating a bone defect in accordance with embodiments of the disclosure, showing a biodegradable sleeve, a fixation member, and a plurality of screws of the device in relation to a proximal bone structure and a distal bone structure in accordance with an example use of the device.
Figure 3B:
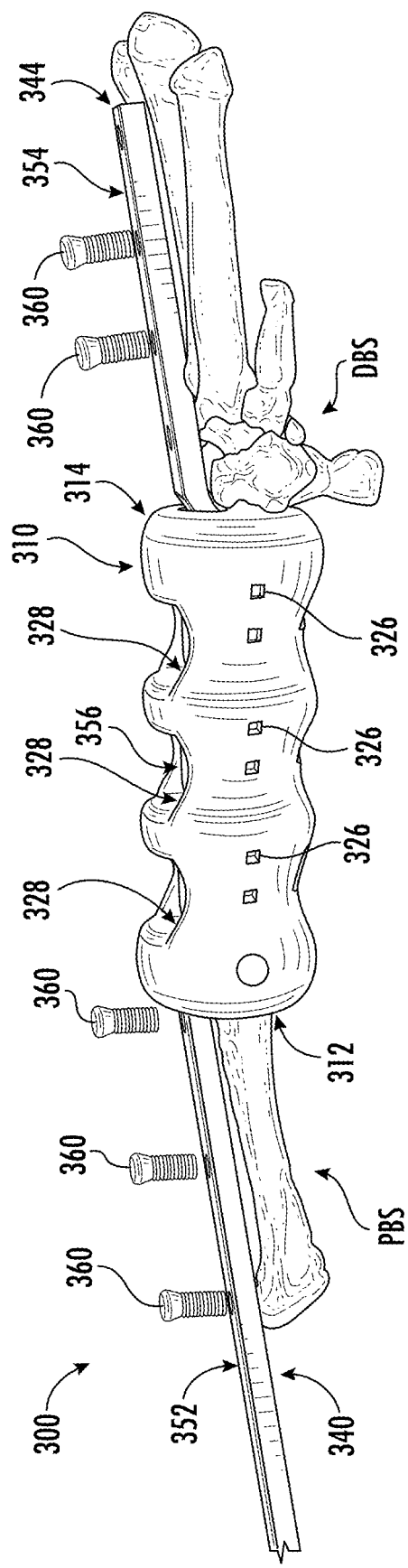
FIG. 3B is a perspective view of the device of FIG. 3A, showing the biodegradable sleeve, the fixation member, and the screws in relation to the proximal bone structure and the distal bone structure.
Figure 3C:
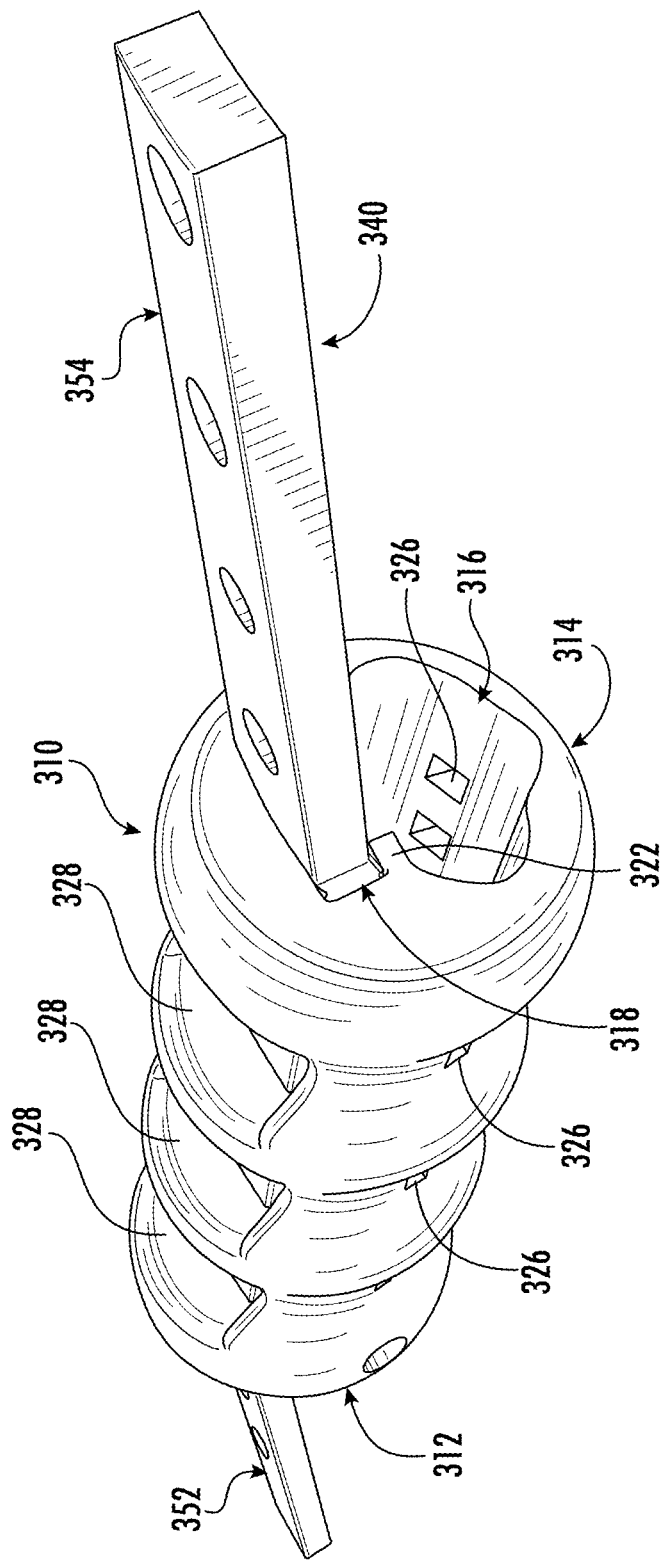
FIG. 3C is a perspective view of a portion of the device of FIG. 3A, showing the fixation member coupled to the biodegradable sleeve.
Figure 3D:
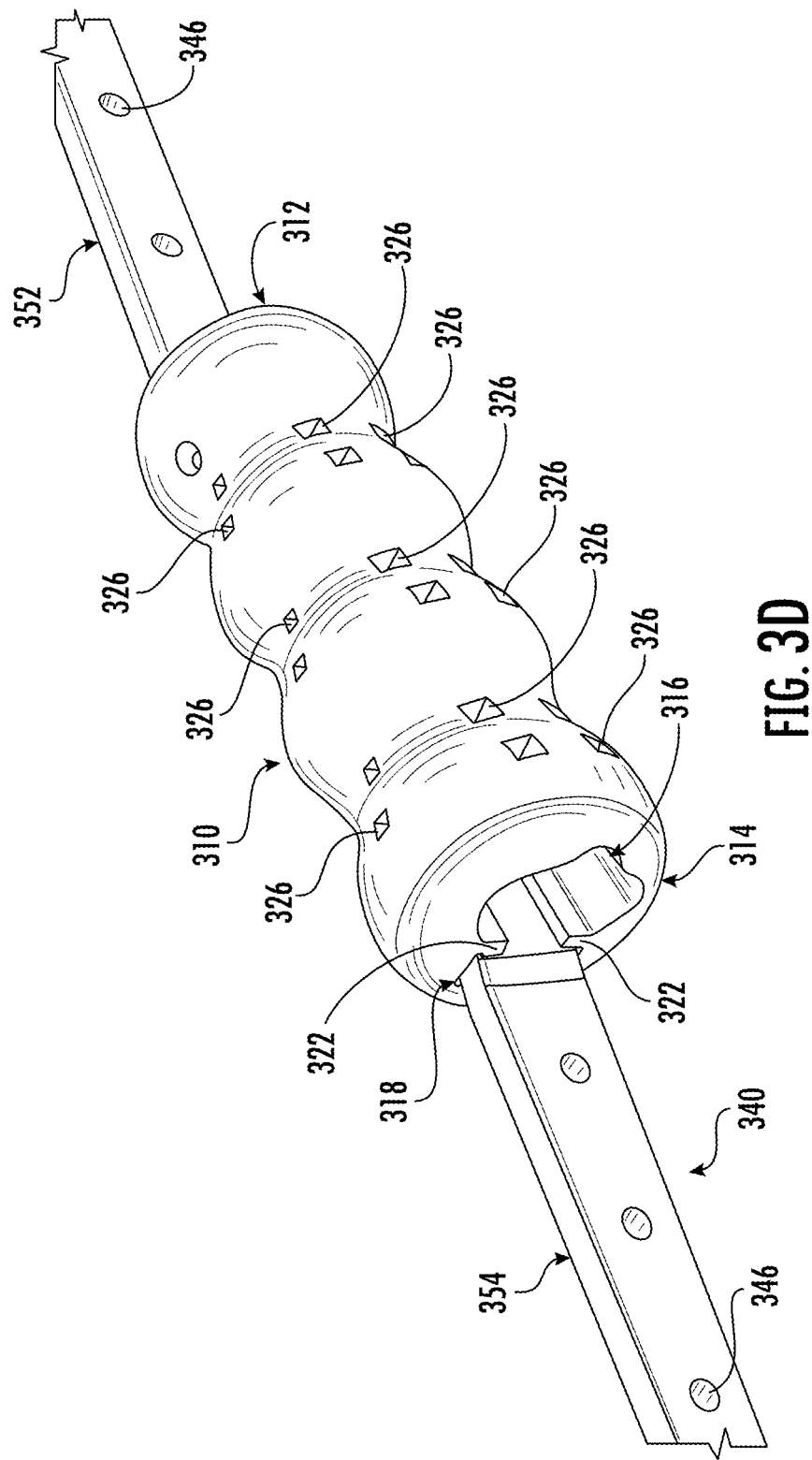
FIG. 3D is a perspective view of a portion of the device of FIG. 3A, showing the fixation member coupled to the biodegradable sleeve.
Figure 3E:
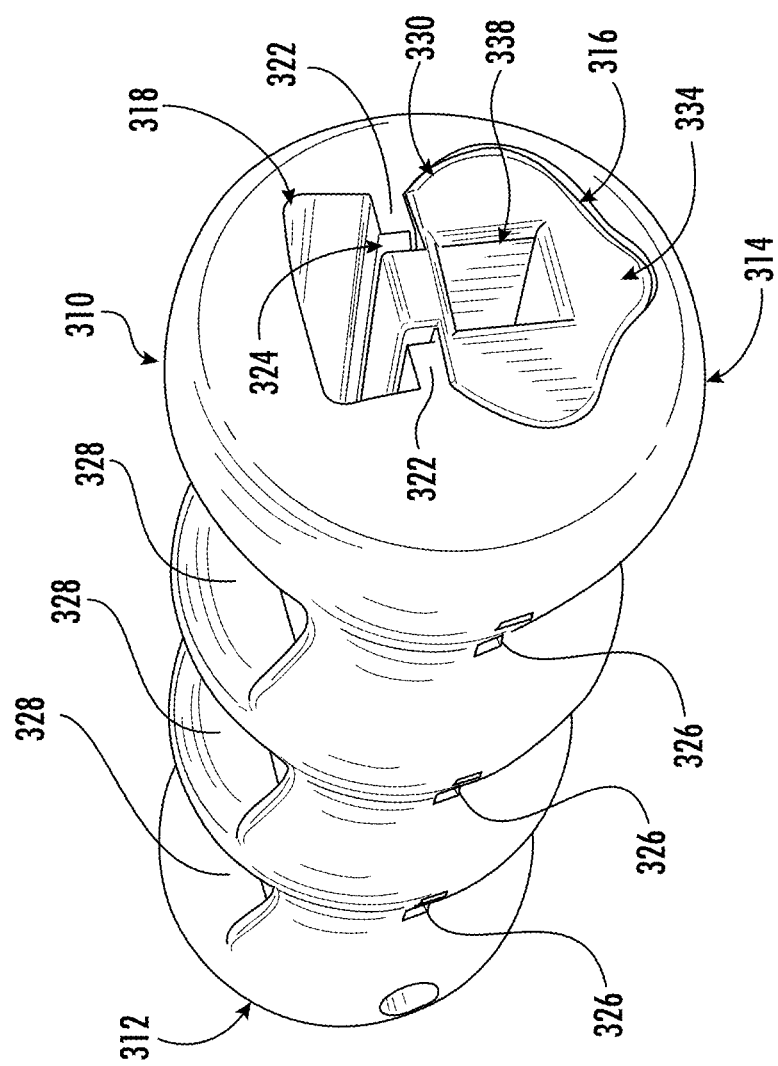
FIG. 3E is a perspective view of a portion of the device of FIG. 3A, showing a biodegradable osteogenic scaffold of the device positioned within the biodegradable sleeve.
Figure 3F:
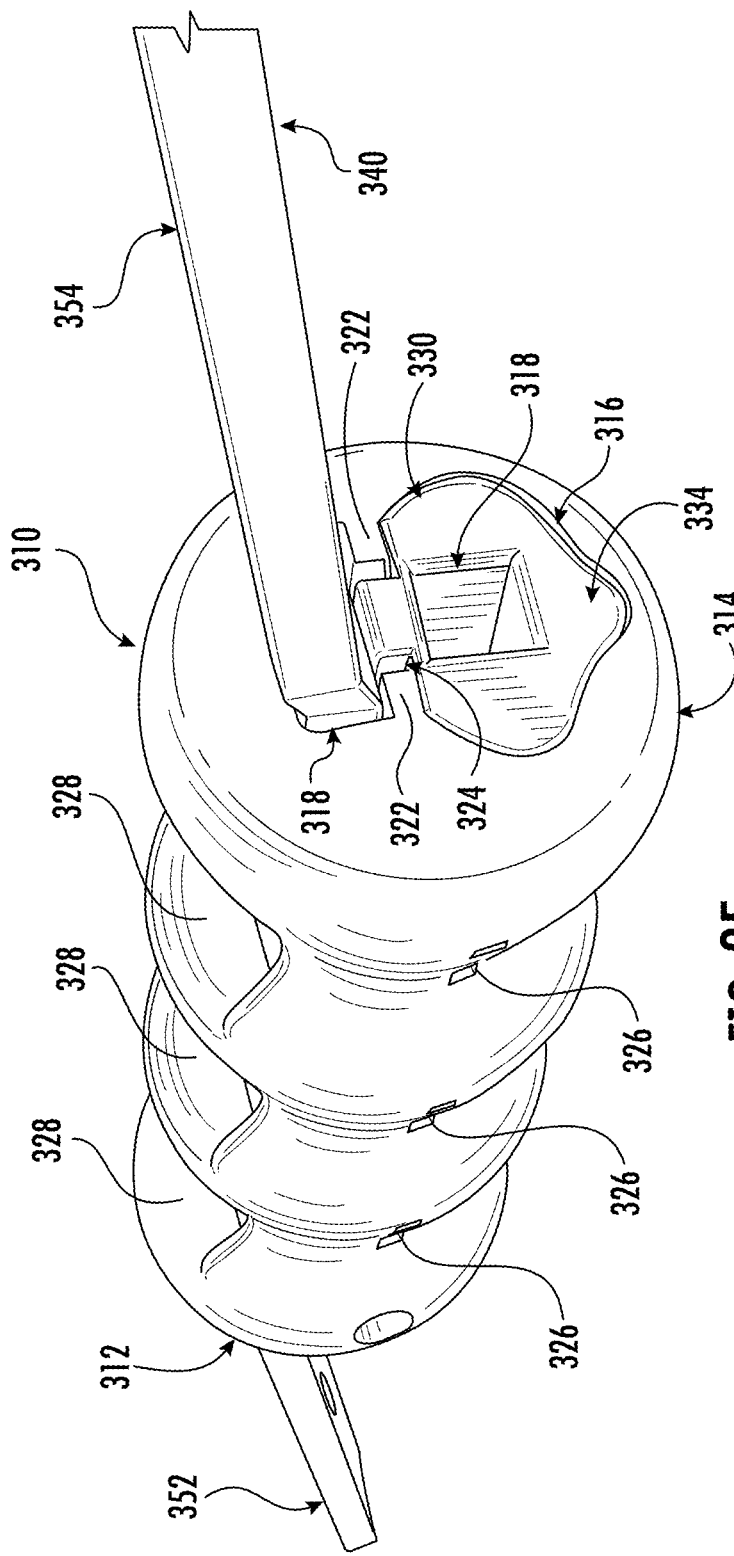
FIG. 3F is a perspective view of a portion of the device of FIG. 3A, showing the fixation member coupled to the biodegradable sleeve and the biodegradable osteogenic scaffold positioned within the biodegradable sleeve.

FIGS. 3A-3F illustrate another example device 300 for treating a bone defect, such as a critical-sized bone defect, of a veterinary or human patient. In some instances, the device 300 may be used to treat an epiphyseal defect. In other instances, the device 300 may be used to treat a segmental defect or a mandibular defect. Because components of the device 300 may be 3D printed according to patient anatomy, they can be appropriately configured to any surgical case. FIGS. 3A and 3B show the device 300 positioned relative to a proximal bone structure PBS and a distal bone structure DBS for treating an epiphyseal defect. As shown, the device 300 may include a biodegradable sleeve 310, a biodegradable osteogenic scaffold 330, a fixation member 340, and a plurality of screws 360. It will be appreciated that the size and shape of the respective components of the device 300 may be varied to accommodate a particular patient and the particular defect being treated. As discussed below, in some embodiments, the biodegradable sleeve 310 and the biodegradable osteogenic scaffold 330 may be fabricated as patient-specific components. For example, these components may be 3D printed based on CT scans of the patient's limb. In some embodiments, the fixation member 340 may be a commercially-available component used in accordance with the standard of care, with the size of the fixation member 340 being selected to accommodate the patient and defect to be treated.

As shown, the biodegradable sleeve 310 may be formed as an elongate structure having a proximal end 312 and a distal end 314 disposed opposite one another along the longitudinal axis of the biodegradable sleeve 310. In some embodiments, as shown, the proximal end 312 may be shape-matched to a distal portion of the proximal bone structure PBS of the patient, and the distal end 314 may be shape matched to a proximal portion of the distal bone structure DBS of the patient. For example, for an epiphyseal defect, the proximal end 312 may be shape-matched to the remaining host radius, and the distal end 314 may be shape-matched to the radial carpus. In some embodiments, as shown, the biodegradable sleeve 310 may have a generally circular cross-sectional shape (i.e., taken perpendicular to the longitudinal axis of the biodegradable sleeve 310). The biodegradable sleeve 310 may include a first passage 316 extending from the proximal end 312 to the distal end 314 and configured for receiving the biodegradable osteogenic scaffold 330 therein. As shown, the shape and size of the first passage 316 may correspond to the shape and size of the biodegradable osteogenic scaffold 330. The biodegradable sleeve 310 also may include a second passage 318 extending from the proximal end 312 to the distal end 314 and configured for receiving a portion of the fixation member 340 therein. As shown, the shape and size of the second passage 318 may correspond to the shape and size of the fixation member 340. In some embodiments, as shown, the biodegradable sleeve 310 may include a pair of support ribs 322 disposed between the first passage 316 and the second passage 318 and extending from the proximal end 312 to the distal end 314 of the biodegradable sleeve 310. As shown, a gap 324 may be defined between the ribs 322 such that the first passage 316 is in communication with the second passage 318 through the gap 324. In some embodiments, as shown, the biodegradable sleeve 310 may include a plurality of apertures 326 disposed along one or more sides of the biodegradable sleeve 310 and extending from an outer surface of the biodegradable sleeve 310 to the first passage 316. In this manner, the apertures 326 may be configured for controlling transcortical perfusion during use of the device 300. In some embodiments, the apertures 326 may be omitted to prevent transcortical perfusion through the biodegradable sleeve 310. In some embodiments, as shown, the biodegradable sleeve 310 may include a plurality of openings 328 disposed along a side of the biodegradable sleeve 310 and extending from an outer surface of the biodegradable sleeve 310 to the second passage 318. The openings 328 may expose respective portions of the fixation member 340 when the fixation member 340 is coupled to the biodegradable sleeve 310 and may be configured for receiving respective collagen sponges carrying one or more bioactive agents therein, such as an antibiotic to inhibit infection, during use of the device 300. In some embodiments, the biodegradable sleeve 310 may be formed of polycaprolactone or a composite comprising a calcium phosphate and polycaprolactone. Other suitable biocompatible and biodegradable materials may be used for the biodegradable sleeve 310 in other embodiments.

The biodegradable osteogenic scaffold 330 may be formed as an elongate structure having a proximal end 332 and a distal end 334 disposed opposite one another along the longitudinal axis of the biodegradable osteogenic scaffold 330. In some embodiments, the biodegradable osteogenic scaffold 330 may have a gyroid topology (similar to that depicted in FIG. 2C), with a plurality of interconnected pores. Other porous topologies of the biodegradable osteogenic scaffold 330 may be used in other embodiments. In some embodiments, the biodegradable osteogenic scaffold 330 may have a porosity of 70%. In some embodiments, as shown, the biodegradable osteogenic scaffold 330 may include a central passage 338 extending from the proximal end 332 to the distal end 334 and configured for receiving a collagen sponge carrying rhBMP-2 therein to facilitate bone growth during use of the device 300. In some embodiments, the length of the biodegradable osteogenic scaffold 330 may be less than the length of the biodegradable sleeve 310. In this manner, the biodegradable osteogenic scaffold 330 may be positioned entirely within the biodegradable sleeve 310 during use of the device 300. As discussed above, the biodegradable osteogenic scaffold 330 may be received within the first passage 316 of the biodegradable sleeve 310. In some embodiments, as shown, a portion of the biodegradable osteogenic scaffold 330 may extend into the gap 324 of the biodegradable sleeve 310. In some embodiments, the biodegradable osteogenic scaffold 330 may be formed of a calcium phosphate, such as HAp or β-TCP. In some embodiments, the biodegradable osteogenic scaffold 330 may be formed of a calcium phosphate-based material or a composite comprising a calcium phosphate and a polymer. Other suitable biocompatible, biodegradable, and osteogenic materials may be used for the biodegradable osteogenic scaffold 330 in other embodiments.

The fixation member 340 may be formed as an elongate structure having a proximal end 342 and a distal end 344 disposed opposite one another along the longitudinal axis of the fixation member 340. According to various embodiments, the fixation member 340 may be a fixation plate, a fixation rod, a locking plate, a locking rod, or other type of suitable structure for fixation of bone structures. In some embodiments, as shown, the fixation member 340 may have a rectangular cross-sectional shape (i.e., taken perpendicular to the longitudinal axis of the fixation member 340). As discussed below, the fixation member 340 may be coupled to the biodegradable sleeve 310 by sliding the biodegradable sleeve 310 onto the fixation member 340 such that the fixation member 340 extends through the second passage 318. As shown, the fixation member 340 may include a plurality of screw holes 346 extending therethrough and spaced apart from one another along the length of the fixation member 340. As discussed below, the screw holes 346 may be used to facilitate connection of the fixation member 340 to the proximal bone structure PBS and the distal bone structure DBS using the screws 360. The fixation member 340 may include a proximal end portion 352, a distal end portion 354, and an intermediate portion 356. As shown, when the fixation member 340 is coupled to the biodegradable sleeve 310, the proximal end portion 352 may extend beyond the proximal end 312 of the biodegradable sleeve 310, the distal end portion 354 may extend beyond the distal end 314 of the biodegradable sleeve 310, and the intermediate portion 356 may be positioned within the second passage 318 of the biodegradable sleeve 310. As shown, the proximal end portion 352 may include a plurality of the screw holes 346 to facilitate connection of the fixation member 340 to the proximal bone structure PBS, and the distal end portion 354 may include a plurality of the screw holes 346 to facilitate connection of the fixation member 340 to the distal bone structure DBS. In some embodiments, the intermediate portion 356 may be devoid of any screw holes 346. In some embodiments, the intermediate portion 356 may include a plurality of the screw holes 346, which may be filled with respective plugs to prevent bone growth therein during use of the device 300. The fixation member 340 may be formed of any suitable biocompatible, non-biodegradable material such that the fixation member 340 may be removed from the patient after the bone defect has healed and the biodegradable sleeve 310 and the biodegradable osteogenic scaffold 330 have degraded. According to various embodiments, the fixation member 340 may be formed of a metal, a polymeric material, a ceramic material, a composite material, or other suitable material for fixation of bone structures.

As noted above, the biodegradable sleeve 310 and the biodegradable osteogenic scaffold 330 may be fabricated as patient-specific components. In some embodiments, CT scans of the patient's limb may be used to fabricate the biodegradable sleeve 310 and the biodegradable osteogenic scaffold 330 for the patient. In some embodiments, a series of two-dimensional DICOM images of the full extent of the limb may be imported (e.g., using InVesalius) and segmented to create high-resolution digital models of the radius, ulna, manus, and metacarpals of the patient. The images then may be segmented based on Hounsfield attenuation values, and surface representations of the bone may be generated and then imported (e.g., into Fusion 360) where 3D models of the components may be created for 3D printing. In some embodiments, finite element analysis (FEA) may be used to investigate the ideal design parameters of the biodegradable sleeve 310 and the overall device 300, with and without the fixation member 340, to determine optimal geometry of the components and features thereof. Parameters such as wall thickness and mechanical properties such as structural modulus may be simulated to optimize the design of the device 300 prior to fabrication. In some embodiments, the CT scans also may be used to fabricate cutting guides to assure accurate surgical resections to match the geometry of the device 300.

The biodegradable osteogenic scaffold 330 may be 3D printed using existing methods. In some embodiments, a photopolymer comprised of ethylene glycol dimethacrylate (EDGMA) and other polymers may be mixed with hydroxyapatite (HAp) particles into a shear-thinning slurry using a planetary ball mill. Slurries of 41 vol % HAp may be transferred to a syringe and 3D printed on 3D printer, such as a HyRel Engine SR printer with a 0.413 mm nozzle inner diameter, using a combination of viscous extrusion and photopolymer processes. The photopolymerization reaction may be initiated by continuous exposure of the deposited roads to a near-UV light source (405 nm wavelength), causing polymerization and hardening of the continuous phase, layer-by-layer. The sintered biodegradable osteogenic scaffold 330 may be non-cytotoxic. After printing, the biodegradable osteogenic scaffold 330 may undergo a two-step sintering process to eliminate the polymeric content and consolidate the HAp particles. In some embodiments, the printed biodegradable osteogenic scaffold 330 may be heated at 5° C./min up to 500° C. and held for 1 h, and then sintered at a heating rate of 15° C./min, up to 1150° C. and held for 5 h. This process may confer the sintered HAp structures with suitable mechanical properties. In some embodiments, the biodegradable sleeve 310 may be fabricated using a thermal process on a melt extrusion 3D printer (e.g., Prusa i3-MK3, Budapest, Hungary). PCL filament may be extruded by regulated ram pressure through a Flexion head. The extruded PCL may cool on a build plate to fabricate the components, which then may cool to room temperature. Prints may be oriented to maximize part strength and minimize support material.

The device 300 may be used to treat a bone defect, such as a critical-sized bone defect, extending between a proximal bone structure PBS and a distal bone structure DBS of a patient. In some embodiments, as shown in FIGS. 3A and 3B, the bone defect may be an epiphyseal defect. In some embodiments, the bone defect may be a segmental defect. A method of using the device 300 for treating the bone defect generally may include resecting a region of bone between the proximal bone structure PBS and the distal bone structure DBS and encompassing the bone defect, positioning the biodegradable osteogenic scaffold 330 within the biodegradable sleeve 310, coupling the biodegradable sleeve 310 to the fixation member 340, positioning the biodegradable sleeve 310 between the proximal bone structure PBS and the distal bone structure DBS, and attaching the fixation member 340 to each of the proximal bone structure PBS and the distal bone structure DBS.

In some embodiments, the region of bone may be resected using one or more cutting guides fabricated based on CT scans of the patient's limb. For an epiphyseal defect, approximately 40% of the distal radius may be removed, along with a slightly larger section of the ulna to enable insertion of the device 300. In some embodiments, the biodegradable osteogenic scaffold 330 may be treated with one or more bioactive agents to facilitate bone growth or angiogenesis before positioning the biodegradable osteogenic scaffold 330 within the biodegradable sleeve 310. For example, the biodegradable osteogenic scaffold 330 may be treated with rhBMP-2 to facilitate bone growth and/or VEGF to facilitate angiogenesis. In some embodiments, one or more collagen sponges containing the one or more bioactive agents may be inserted within the central passage 338 of the biodegradable osteogenic scaffold 330. In some embodiments, the biodegradable osteogenic scaffold 330 may be positioned within the biodegradable sleeve 310 such that the proximal end 332 of the biodegradable osteogenic scaffold 330 is offset from the proximal end 312 of the biodegradable sleeve 310, and a distal portion of the proximal bone structure PBS may be inserted into the first passage 316 of the biodegradable sleeve 310 and in contact with the proximal end 332 of the biodegradable osteogenic scaffold 330. For an epiphyseal defect, a distal portion of the remaining host radius may be inserted into the first passage 316 of the biodegradable sleeve 310 and in contact with the proximal end 332 of the biodegradable osteogenic scaffold 330. In some embodiments, the biodegradable osteogenic scaffold 330 may be positioned within the biodegradable sleeve 310 such that the distal end 334 of the biodegradable osteogenic scaffold 330 is flush with the distal end 314 of the biodegradable sleeve 310, and a proximal portion of the distal bone structure DBS may be positioned in close contact with the distal end 334 of the biodegradable osteogenic scaffold 330 and the distal end 314 of the biodegradable sleeve 310. For an epiphyseal defect, the proximal end of the carpus may be positioned in close contact with the distal end 334 of the biodegradable osteogenic scaffold 330 and the distal end 314 of the biodegradable sleeve 310. In some embodiments, the biodegradable osteogenic scaffold 330 may be positioned within the biodegradable sleeve 310 such that the distal end 334 of the biodegradable osteogenic scaffold 330 is offset from the distal end 314 of the biodegradable sleeve 310, and a proximal portion of the distal bone structure DBS may be inserted into the first passage 316 of the biodegradable sleeve 310 and in contact with the distal end 334 of the biodegradable osteogenic scaffold 330.

In some embodiments, the biodegradable sleeve 310 may be coupled to the fixation member 340 before the biodegradable sleeve 310 is positioned between the proximal bone structure PBS and the distal bone structure DBS. In some embodiments, the biodegradable sleeve 310 may be coupled to the fixation member 340 by sliding the biodegradable sleeve 310 over the fixation member 340 such that the intermediate portion 356 of the fixation member 340 is positioned within the second passage 318, the proximal end portion 352 of the fixation member 340 extends beyond the proximal end 312 of the biodegradable sleeve 310, and the distal end portion 354 of the fixation member 340 extends beyond the distal end 314 of the biodegradable sleeve 310. In some embodiments, the proximal end portion 352 of the fixation member 340 may be attached to the proximal bone structure PBS using a first plurality of the screws 360, and the distal end portion 354 of the fixation member 340 may be attached to the distal bone structure DBS using a second plurality of the screws 360. For an epiphyseal defect, the proximal end portion 352 of the fixation member 340 may be attached to the remaining host radius, and the distal end portion 354 of the fixation member 340 may be attached to the third metacarpal. In some embodiments, the biodegradable sleeve 310 may be coupled to the fixation member 340 and positioned between the proximal bone structure PBS and the distal bone structure DBS after the fixation member 340 is attached to the proximal bone structure PBS but before the fixation member 340 is attached to the distal bone structure DBS. In other words, the proximal end portion 352 of the fixation member 340 may be attached to the proximal bone structure PBS, the biodegradable sleeve 310 then may be slid onto the fixation member 340 from the proximal end 342 toward the distal end 344 and positioned between the proximal bone structure PBS and the distal bone structure DBS, and the distal end portion 354 of the fixation member 340 then may be attached to the distal bone structure DBS.

Although specific embodiments of the disclosure have been described, one of ordinary skill in the art will recognize that numerous other modifications and alternative embodiments are within the scope of the disclosure. Further, while various illustrative implementations have been described in accordance with embodiments of the disclosure, one of ordinary skill in the art will appreciate that numerous other modifications to the illustrative implementations described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. A method for treating a bone defect extending between a proximal bone structure and a distal bone structure of a patient, the method comprising: resecting a region of bone between the proximal bone structure and the distal bone structure and encompassing the bone defect; positioning a biodegradable osteogenic scaffold within a biodegradable sleeve, wherein the biodegradable osteogenic scaffold defines a plurality of interconnected pores; coupling the biodegradable sleeve to a fixation member, wherein the biodegradable sleeve comprises: a first passage extending from a proximal end to a distal end of the biodegradable sleeve and configured for receiving the biodegradable osteogenic scaffold therein; and a second passage extending from the proximal end to the distal end of the biodegradable sleeve and configured for receiving a portion of the fixation member therein; positioning the biodegradable sleeve between the proximal bone structure and the distal bone structure; and attaching the fixation member to each of the proximal bone structure and the distal bone structure.

2. The method of claim 1, wherein coupling the biodegradable sleeve to the fixation member comprises sliding the biodegradable sleeve onto the fixation member.

3. The method of claim 1, wherein positioning the biodegradable sleeve between the proximal bone structure and the distal bone structure comprises:
   inserting a distal end portion of the proximal bone structure into a proximal end of the biodegradable sleeve such that the distal end portion contacts the biodegradable osteogenic scaffold; and
   inserting a proximal end portion of the distal bone structure into a distal end of the biodegradable sleeve such that the proximal end portion contacts the biodegradable osteogenic scaffold.

4. The method of claim 1, wherein attaching the fixation member to each of the proximal bone structure and the distal bone structure comprises:
   attaching the fixation member to the proximal bone structure using a first plurality of screws; and
   attaching the fixation member to the distal bone structure using a second plurality of screws.

5. The method of claim 1, further comprising treating the biodegradable osteogenic scaffold with one or more bioactive agents to facilitate bone growth or angiogenesis.

6. The method of claim 1, further comprising treating the biodegradable sleeve and the fixation member with an antibiotic to inhibit infection.

7. The method of claim 1, further comprising:
   obtaining computed tomography scans of the patient; and
   fabricating the biodegradable osteogenic scaffold and the biodegradable sleeve based at least in part on the computed tomography scans.

8. The method of claim 7, further comprising fabricating a cutting guide based at least in part on the computed tomography scans, wherein resecting the region of bone between the proximal bone structure and the distal bone structure and encompassing the bone defect comprises resecting the region of bone using the cutting guide.

9. The method of claim 1, wherein the biodegradable osteogenic scaffold is formed of a calcium phosphate-based material or a composite comprising a calcium phosphate and a polymer, and wherein the biodegradable sleeve is formed of polycaprolactone or a composite comprising a calcium phosphate and polycaprolactone.

10. The method of claim 1, further comprising detaching the fixation member from the proximal bone structure and the distal bone structure and removing the fixation member from the patient after the bone defect has healed and the biodegradable osteogenic scaffold and the biodegradable sleeve have degraded.

11. A device for treating a bone defect extending between a proximal bone structure and a distal bone structure of a patient, the device comprising: a biodegradable sleeve configured for positioning between the proximal bone structure and the distal bone structure; a biodegradable osteogenic scaffold configured for positioning within the biodegradable sleeve, wherein the biodegradable osteogenic scaffold defines a plurality of interconnected pores; and a fixation member configured for coupling to the biodegradable sleeve and attaching to each of the proximal bone structure and the distal bone structure, wherein the biodegradable sleeve comprises: a first passage extending from a proximal end to a distal end of the biodegradable sleeve and configured for receiving the biodegradable osteogenic scaffold therein; and a second passage extending from the proximal end to the distal end of the biodegradable sleeve and configured for receiving a portion of the fixation member therein.

12. The device of claim 11, wherein the biodegradable sleeve further comprises support ribs disposed between the first passage and the second passage and extending from the proximal end to the distal end of the biodegradable sleeve, and wherein the first passage is in communication with the second passage through a gap defined between the support ribs.

13. The device of claim 12, wherein a portion of the biodegradable osteogenic scaffold extends into the gap when the biodegradable osteogenic scaffold is positioned within the biodegradable sleeve.

14. The device of claim 11, wherein the first passage is further configured for receiving a distal end portion of the proximal bone structure and a proximal portion of the distal bone structure therein.

15. The device of claim 11, wherein the biodegradable sleeve further comprises a plurality of apertures disposed along one or more sides of the biodegradable sleeve and extending from an outer surface of the biodegradable sleeve to the first passage, and wherein the apertures are configured for controlling transcortical perfusion.

16. The device of claim 11, wherein the biodegradable sleeve further comprises a plurality of openings disposed along a side of the biodegradable sleeve and extending from an outer surface of the biodegradable sleeve to the second passage, and wherein the openings expose respective portions of the fixation member when the fixation member is coupled to the biodegradable sleeve and are configured for receiving respective collagen sponges carrying an antibiotic therein.

17. The device of claim 11, wherein the biodegradable osteogenic scaffold comprises a central passage extending from a proximal end to a distal end of the biodegradable osteogenic scaffold and configured for receiving a collagen sponge carrying rhBMP-2 or VEGF therein.

18. The device of claim 11, wherein the fixation member comprises:
- a proximal portion configured for extending beyond the proximal end of the biodegradable sleeve when the fixation member is coupled to the biodegradable sleeve;
- a distal portion configured for extending beyond the distal end of the biodegradable sleeve when the fixation member is coupled to the biodegradable sleeve; and
- an intermediate portion configured for positioning within the second passage when the fixation member is coupled to the biodegradable sleeve.

19. The device of claim 11, wherein the biodegradable osteogenic scaffold is formed of a calcium phosphate-based material or a composite comprising a calcium phosphate and a polymer, and wherein the biodegradable sleeve is formed of polycaprolactone or a composite comprising a calcium phosphate and polycaprolactone.

* * * * *